United States Patent
El-Agnaf et al.

(10) Patent No.: US 8,778,334 B2
(45) Date of Patent: Jul. 15, 2014

(54) METHOD OF IDENTIFYING WHETHER OR NOT AN INDIVIDUAL HAS PARKINSON'S DISEASE RATHER THAN ANOTHER NEURODEGENERATIVE DISEASE

(75) Inventors: Omar El-Agnaf, Al Ain (AE); Lucilla Parnetti, Perugia (IT); Paolo Calabresi, Perugia (IT)

(73) Assignees: United Arab Emirates University, Al Ain (AE); Universita Degli Studi di Perugia, Perugia (IT)

( * ) Notice: Subject to any disclaimer, the term of this patent is extended or adjusted under 35 U.S.C. 154(b) by 0 days.

(21) Appl. No.: 13/807,963

(22) PCT Filed: Jul. 6, 2011

(86) PCT No.: PCT/GB2011/001026
§ 371 (c)(1),
(2), (4) Date: Mar. 25, 2013

(87) PCT Pub. No.: WO2012/004566
PCT Pub. Date: Jan. 12, 2012

(65) Prior Publication Data
US 2013/0183278 A1    Jul. 18, 2013

(30) Foreign Application Priority Data
Jul. 6, 2010  (GB) .................................. 1011420.5

(51) Int. Cl.
*A61K 38/43* (2006.01)
(52) U.S. Cl.
USPC ....................................................... 424/94.1
(58) Field of Classification Search
USPC .............. 424/9.1, 94.1; 514/17.7; 530/388.2, 530/389.1
See application file for complete search history.

(56) References Cited

U.S. PATENT DOCUMENTS

| 2011/0159527 A1* | 6/2011 | Schlossmacher et al. ... 435/7.92 |
| 2012/0190652 A1* | 7/2012 | El-Agnaf ...................... 514/152 |
| 2012/0282642 A1* | 11/2012 | Bateman et al. ............... 435/23 |
| 2013/0177549 A1* | 7/2013 | Schlossmacher et al. . 424/130.1 |

FOREIGN PATENT DOCUMENTS

| WO | 00/02053 A2 | 1/2000 |
| WO | 2009/152607 A1 | 12/2003 |

OTHER PUBLICATIONS

Reesink, F. et al. CSF Alpha-Synuclein Does Not Discriminate Dementia with Lewy Bodies from AD. J of AD 22(1)87-95, 2010.*
Parnetti, L. et al. Cerebrospinal Fluid Tau/Alpha-Synuclein Ratio in PD and Degenerative Dementias. Movement Disorders 26(8)1428-35, 2011.*
Johansen et al., "Biomarkers: Parkinson disease with dementia and dementia with Lewy bodies," Parkinsonism and related disorders, Jun. 2010, vol. 16, No. 5, pp. 307-315.
Ohrfelt et al., "Cerebrospinal fluid alpha-synuclein in neurodegenerative disorders—A marker of synapse loss?," Neuroscience Letters, Feb. 2009, vol. 450, No. 3, pp. 332-335.
Parnetti et al., "Cerebrosponal fluid Biomarkers in Parkinson's Disease with Dementia and Dementia with Lewy Bodies," Biological Psychiatry, Nov. 2008, vol. 64, No. 10, pp. 850-855.
International Search Report and Written Opinion, Sep. 14, 2011, PCT application No. PCT/GB2011/001026, 7 pages.

* cited by examiner

*Primary Examiner* — Ralph Gitomer
(74) *Attorney, Agent, or Firm* — Kilpatrick Townsend & Stockton LLP

(57) ABSTRACT

The present invention relates to method of identifying whether or not an individual has Parkinson's disease (PD). In particular, the invention relates to a method for identifying whether or not an individual has PD as opposed to another neurodegenerative disease. The method of the invention comprises measuring the concentration of α-synuclein (α-syn) and the concentration of unphosphorylated tau (tau) and/or phosphorylated tau (p-tau) in a cerebrospinal fluid sample taken from an individual. The method also comprises calculating the ratio of the concentration of tau and/or p-tau to the concentration of α-syn, and thereby determining whether or not the individual has PD.

10 Claims, 2 Drawing Sheets

METHOD OF IDENTIFYING WHETHER OR NOT AN INDIVIDUAL HAS PARKINSON'S DISEASE RATHER THAN ANOTHER NEURODEGENERATIVE DISEASE

CROSS-REFERENCES TO RELATED APPLICATIONS

This application is a 371 of International Application No. PCT/GB2011/001026 filed Jul. 6, 2011, which claims benefit of foreign priority to GB 1011420.5, filed Jul. 6, 2010, each of which is incorporated by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The present invention relates to method of identifying whether or not a patient has Parkinson's disease (PD). In particular, the invention relates to a method for identifying whether or not an individual has PD rather than a different neurodegenerative disorder which is not PD.

BACKGROUND OF THE INVENTION

Neurodegenerative disorders are often classified based on abnormalities in α-synuclein (α-syn) or tau protein, such abnormalities typically being identified during a pathological analysis. As a result, a neurodegenerative disorder is typically classified as either a synucleinopathy or a tauopathy, with the two categories often being viewed as two distinct types of clinical and pathological entity This view is consistent with the most obvious clinical manifestations of common disorders in each category. For example, the most common disorder classed as a synucleinopathy, Parkinson's Disease (PD), is characterized by extrapyramidal motor dysfunction, whereas the most common tauopathy, Alzheimer's Disease (AD) is defined by dementia, as is another relatively common tauopathy, Frontotemporal Dementia (FTD).

Despite this, there are considerable overlaps in the clinical symptoms of the synucleinopathies and tauopathies. For example, PD patients frequently have dementia, and AD and FTD patients often manifest parkinsonism. Dementia with Lewy bodies (DLB), although defined as a synucleinopathy, exemplifies the existence of a continuum between the clinical symptoms of the synucleinopathies and of the tauopathies. This continuum leads to difficulties when attempting to accurately diagnose a patient, particularly at an early stage in their illness.

Accordingly, there is a need for the development of a reliable diagnostic test which can discriminate between different neurological disorders.

BRIEF SUMMARY OF THE INVENTION

There is a growing amount of evidence supporting a functional and morphological overlap between the synucleinopathies and the tauopathies. For example:

(i) phosphorylated tau and α-synuclein have been found in synaptic-enriched fractions in several synucleinopathies;

(ii) a specific colocalization of neurofibrillary tangles and Lewy bodies has been described in a family with progressive aphasia;

(iii) in the brain of some patients carrying progranulin c.709-2A>G mutation, a diffuse α-syn pathology has been documented;

(iv) one case of frontotemporal lobar degeneration with ubiquitinated tau-negative inclusions and diffuse cortical α-syn pathology has been described;

(v) members of San Francisco family A, affected by 17qlinked FTD and amyotrophic lateral sclerosis without tau mutations, showed in their brains tau and α-syn inclusions, thus combining the features of an α-synucleinopathy and tauopathy.

Moreover, mutations in LRRK2 known to cause Parkinsonism are associated not only with dopaminergic neuronal degeneration, but also with the accumulation of α-syn, tau, or both proteins. Other shared genetic features between tauopathies and synucleinopathies also exist. The overlap in the clinical and pathological features of tauopathies and synucleinopathies raises the possibility that the tau protein may be important in PD pathogenesis. Recently, it has been reported that genetic variability in tau gene (MAPT) confers susceptibility to PD.

As a candidate biomarker of synucleinopathies, namely PD and dementia with Lewy bodies (DLB), α-syn determination in cerebrospinal fluid (CSF) might improve the clinical diagnostic accuracy for these neurodegenerative conditions. However, since the development of assays for CSF α-syn measurement is quite recent, only a few studies on this issue are available yet and all of them are retrospective. One study reported that PD patients show significantly lower CSF α-syn levels as compared to controls and that such a reduction is correlated to the severity of illness. Another study found lower CSF α-synuclein levels in a primary synucleinopathy group (DLB and PD) as compared to AD or non-neurodegenerative control subjects. Conversely, other subsequent reports failed to show any difference in CSF α-syn levels between PD and controls and between DLB and Alzheimer's disease (AD). A further study also failed to show significant differences between DLB and AD, and found an inverse association between CSF α-syn levels and disease duration only in DLB patients.

By contrast, several studies have shown that CSF classical biomarkers (e.g. β amyloid$_{1-42}$, tau, phosphorylated tau) may be useful for early diagnosis of AD. These biomarkers may represent the in vivo expression of the neurodegenerative process taking place in the brain of AD patients even before the clinical onset of dementia. Accordingly, the present inventors considered that, although these biomarkers do not directly contribute to the diagnosis of non-AD dementias, they could provide further information on the physiopathology of neurodegenerative diseases associated with cognitive impairment. In fact, the clinical phenotype of most neurodegenerative disorders, characterized by movement and/or cognitive deficits, may be the consequence of concomitant pathologies, that is Lewy bodies and Alzheimer pathology, resulting from the mutual interaction between α-syn, β-amyloid$_{1-42}$ and tau, during the course of the disease.

Therefore, the inventors hypothesised that a combination of different CSF biomarkers might help in discriminating between these neurodegenerative disorders, especially in the early phase, when the clinical diagnosis is more difficult and its accuracy is crucial, in view of appropriate and timely pharmacological treatment. The inventors have found that, despite the previously reported inconsistencies in reported CSF α-syn levels, evaluation of the ratio of the total concentration of tau in a sample relative to the concentration of α-syn showed significantly lower levels for this ratio in PD patients compared to other pathological groups (P<0.002), including AD, FTD and DLB. Similar results were obtained for the ratio of the concentration of phosphorylated tau (p-tau) in a sample relative to the concentration of α-syn.

Accordingly the present invention provides:

A method of identifying whether or not an individual has Parkinson's Disease (PD) rather than a neurodegenerative disease which is not PD, which method comprises:
(i) measuring the concentration of α-synuclein (α-syn) in a cerebrospinal fluid (CSF) sample taken from the individual;
(ii) measuring the concentration of unphosphorylated tau (tau) and/or phosphorylated (p-tau) present in the sample; and
(iii) calculating the ratio of:

$$\frac{\text{total concentration of tau}}{\text{concentration of } \alpha\text{-syn}} \text{ or } \frac{\text{concentration of } p\text{-tau}}{\text{concentration of } \alpha\text{-syn}}$$

wherein the total concentration of tau is the cumulative concentration of p-tau and tau measured in the sample; and
(iv) thereby determining whether or not the individual has PD.

The invention also provides:

A method of delaying or preventing the onset of PD symptoms in an individual, comprising;
(i) determining whether or not an individual has PD using a method according to the invention; and
(ii) administering to an individual identified in (i) as having PD, a therapeutically effective concentration of an agent that directly or indirectly inhibits α-syn aggregation and/or toxicity, an agent that reduces expression of the α-syn protein, an agent that directly or indirectly enhances or stimulates the degradation of α-syn aggregates, or a neuroprotective agent.

The invention also provides:

A test kit for use in a method for determining whether or not an individual has PD, which test kit comprises means for the detection of α-synuclein, tau and/or p-tau in a sample of CSF.

DETAILED DESCRIPTION OF THE INVENTION

Figure 1:
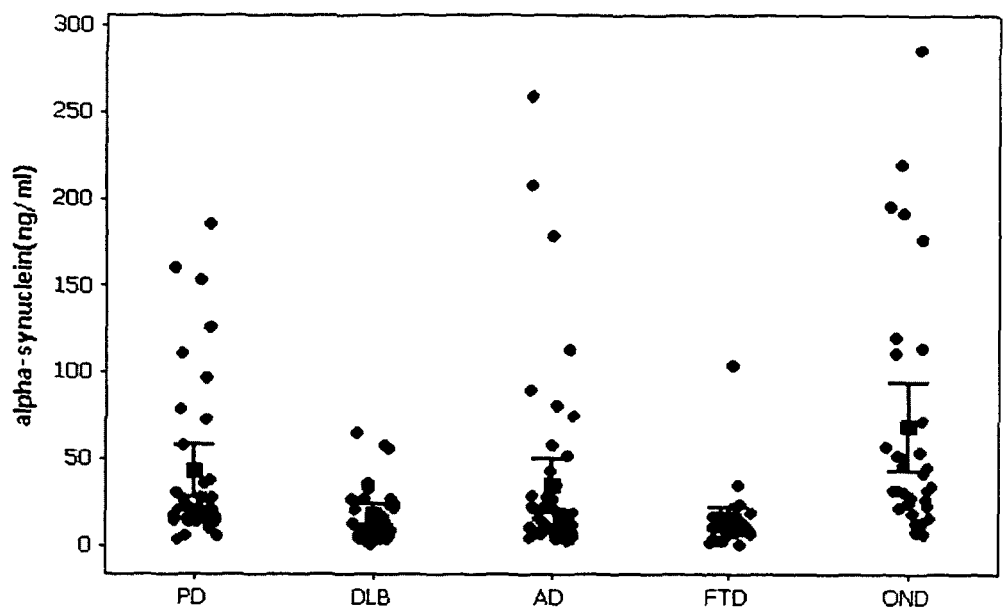
FIG. 1 shows the scatter of CSF α-syn concentrations observed in subjects with Parkinson's Disease (PD), Dementia with Lewy bodies (DLB), Alzheimer's Disease (AD), Frontotemporal Dementia (FTD) and cognitively normal individuals (OND).

The present invention relates to a method of identifying whether or not a subject has PD rather than a neurodegenerative disease or disorder which is not PD. The invention therefore relates to the detection of PD in the individual subject. The individual is typically a mammal. The mammal is typically a human or a domestic mammal such as a horse, a cow, a sheep, a dog or a cat. The individual is preferably a human. The individual may be up to 30, up to 40, up to 50, up to 60 or up to 70 years old. The individual may have an age of 30 to 40, 30 to 50, 30 to 60 or 30 to 70 years. The individual may have an age of 40 to 50, 40 to 60 or 40 to 70 years. The individual may have an age of 50 to 60 or 50 to 70 years.

The individual is typically suspected of being at risk of developing a neurodegenerative disorder. This may be because the individual has a familial history of a neurodegenerative disorder or for other reasons. The individual may have or have been diagnosed with one or more symptoms associated with a clinical diagnosis of a neurodegenerative disorder. The neurodegenerative disorder may be Parkinson's Disease (PD), Alzheimer's Disease (AD), Dementia with Lewy bodies (DLB) or Frontotemporal Dementia (FTD).

As an example, the individual may exhibit one or more of the following symptoms associated with PD:

Primary Motor Symptoms

Present clinical practice typically requires the presence of at least one primary motor symptom for a diagnosis of PD. The primary motor symptoms are:

(i) Resting Tremor: About 70 percent of people with Parkinson's experience a slight tremor, which is often the first identifiable symptom. The tremor is typically in either the hand or foot on one side of the body, or less commonly in the jaw or face. The tremor appears as a "beating" or oscillating movement. The Parkinson's tremor usually appears when a person's muscles are relaxed, hence it is called "resting tremor." Typically the affected body part trembles when it is not doing work, and the tremor subsides when a person begins an action. The tremor often spreads to the other side of the body as the disease progresses, but remains most apparent on the original side of occurrence.

(ii) Bradykinesia (Slow movement): the patient displays markedly slow movement. In addition to slow movement, a person with bradykinesia will typically also have incomplete movement, difficulty initiating movements and difficulty in suddenly stopping ongoing movements. People who have bradykinesia may walk with short, shuffling steps (festination). Bradykinesia and rigidity can occur in the facial muscles, reducing a person's range of facial expressions and resulting in a "mask-like" appearance.

(iii) Rigidity: also called increased muscle tone, means stiffness or inflexibility of the muscles. In rigidity, the muscle tone of an affected limb is always stiff and does not relax, sometimes resulting in a decreased range of motion. For example, a person who has rigidity may not be able to swing his or her arms when walking because the muscles are too tight. Rigidity can cause pain and cramping.

(iv) Postural Instability (Impaired Balance and Coordination): Subjects with PD often experience instability when standing, or have impaired balance and coordination. These symptoms, combined with other symptoms such as bradykinesia, increase the chance of falling. Subjects with balance problems may have difficulty making turns or abrupt movements. The subject may go through periods of "freezing," in which the subject finds it difficult to start walking. Slowness and incompleteness of movement can also affect speaking and swallowing.

Secondary Motor Symptoms

Not all PD subjects will experience secondary motor symptoms. However, most subjects typically exhibit one or more of the following:

Stooped posture, a tendency to lean forward
Dystonia
Fatigue
Impaired fine motor dexterity and motor coordination
Impaired gross motor coordination
Poverty of movement (decreased arm swing)
Akathisia
Speech problems, such as softness of voice or slurred speech caused by lack of muscle control
Loss of facial expression, or "masking"
Micrographia (small, cramped handwriting)
Difficulty swallowing
Sexual dysfunction
Drooling Non-Motor Symptoms A number of non-motor symptoms are associated with PD. However, these symptoms are not specific for PD, and are typically only identified as indicating PD retrospectively. That is, the non-motor symptoms experienced by a subject are not typically recognised as indicating PD until after the presence of primary and secondary motor symptoms has been confirmed. Even so, a PD patient will typically exhibit one or more of the following:

Pain
Dementia or confusion
Sleep disturbances (e.g. REM sleep behaviour disorder (RBD))
Hyposmia
Constipation
Skin problems
Depression
Fear or anxiety
Memory difficulties and slowed thinking
Urinary problems
Fatigue and aching
Loss of energy
Compulsive behavior (e.g. Gambling)
Cramping The individual may or may not have been categorised according to the Hoehn-Yahr scale. The Hoehn-Yahr scale is a commonly used system for describing how the symptoms of Parkinson's disease progress. The scale allocates stages from 0 to 5 to indicate the relative level of disability:

Stage one: Symptoms on one side of the body only.
Stage two: Symptoms on both sides of the body. No impairment of balance.
Stage three: Balance impairment. Mild to moderate disease. Physically independent.
Stage four: Severe disability, but still able to walk or stand unassisted.
Stage five: Wheelchair-bound or bedridden unless assisted.

If categorised, the individual is typically grade 2 or lower on the Hoehn-Yahr scale.

The individual may or may not have been diagnosed with PD according to the UK Parkinson's Disease Society Brain Bank criteria. These criteria are:

Step 1: Diagnosis of Parkinsonian Syndrome
Bradykinesia
At least one of the following
Muscular rigidity
4-6 Hz rest tremor
postural instability not caused by primary visual, vestibular, cerebellar, or proprioceptive dysfunction Step 2: Identification of Features Tending to Exclude Parkinson's Disease as the Cause of Parkinsonism
history of repeated strokes with stepwise progression of parkinsonian features
history of repeated head injury
history of definite encephalitis
oculogyric crises
neuroleptic treatment at onset of symptoms
more than one affected relative
sustained remission
strictly unilateral features after 3 years
supranuclear gaze palsy
cerebellar signs
early severe autonomic involvement
early severe dementia with disturbances of memory, language, and praxis
Babinski sign
presence of cerebral tumor or communication hydrocephalus on imaging study
negative response to large doses of levodopa in absence of malabsorption
MPTP (1-methyl 4-phenyl 1,2,3,6-tetrahydropyridine) exposure Step 3: Identification of Features that Support a Diagnosis of Parkinson's Disease (Three or More in Combination with Step 1 Required for Diagnosis of Definite Parkinson's Disease):
Unilateral onset
Rest tremor present
Progressive disorder
Persistent asymmetry affecting side of onset most
Excellent response (70-100%) to levodopa
Severe levodopa-induced chorea
Levodopa response for 5 years or more
Clinical course of ten years or more The individual may be suspected of being at risk of developing PD because of the presence of one or more factors which increase susceptibility to PD. The individual may have a familial history of PD. Large epidemiological studies demonstrate that people with an affected first-degree relative, such as a parent or sibling, have a two-to-three fold increased risk of developing Parkinson's, as compared to the general population.

The individual may have a mutation or polymorphism in a gene or locus associated with PD. For example, the individual may have a mutation or polymorphism in one of more of the following genes or loci: PARK1 (gene encoding α-synuclein (SNCA)), PARK2 (gene encoding suspected ubiquitin-protein ligase Parkin (PRKN2)), PARK3, PARK4, PARK5 (gene encoding ubiquitin carboxy-terminal hydrolase L1), PARK6 (gene encoding a putative protein kinase (PINK1)), PARK7 (gene encoding DJ-1), or PARK8 (gene encoding leucine-rich repeat kinase 2 (LRRK2)).

The individual may have a mutation or polymorphism in one or more of the genes encoding the following products: Dopamine receptor 2, Dopamine receptor 4, Dopamine transporter, Monoamine oxidase A, Monoamine oxidase B, Catechol-o-methyl-transferase, N-acetyl transferase 2 detoxification enzyme, Apo-lipoprotein E, Glutathione transferase detoxification enzyme T1, Glutathione transferase detoxification enzyme M1, Glutathione transferase detoxification enzyme, or Glutathione transferase detoxification enzyme Z1; and/or in the tRNA Glu mitochondrial gene and/or the Complex 1 mitochondrial gene. Preferably the individual has a mutation or polymorphism in the gene encoding Monoamine oxidase B, and/or N-acetyl transferase 2 detoxification enzyme, and/or Glutathione transferase detoxification enzyme T1 and/or in the tRNA Glu mitochondrial gene.

Environmental risk factors may also be present. To date, epidemiological research has identified rural living, well water, herbicide use and exposure to pesticides as factors that may be linked to PD. Also, MPTP (1-methyl 4-phenyl 1,2,3, 6-tetrahydropyridine) can cause Parkinsonism if injected. The chemical structure of MPTP is similar to the widely used herbicide paraquat and damages cells in a way similar to the pesticide rotenone, as well as some other substances.

As a further example, the individual may exhibit one or more of the following symptoms associated with DLB. The core features of DLB include: 1) fluctuating cognition with great variations in attention and alertness from day to day and hour to hour; 2) recurrent visual hallucinations (observed in 75% of people with DLB); and 3) motor features of parkinsonism. Suggestive symptoms are Rapid eye movement behavior disorder and abnormalities detected in PET or SPECT scans.

For example, the individual may exhibit one or more of the consensus criteria for the clinical diagnosis of probable and possible DLB (McKeith's criteria), which are as follows:
a.) The central feature required for a diagnosis of dementia with Lewy bodies (DLB) is progressive cognitive decline of sufficient magnitude to interfere with normal social or occupational function. Prominent or persistent memory impairment may not necessarily occur in the early stages but is usually evident with progression. Deficits on tests of attention and of frontal-subcortical skills and visuospatial ability may be especially prominent.
b.) Two of the following core features are essential for a diagnosis of probable DLB, one is essential for possible DLB.
i. Fluctuating cognition with pronounced variations in attention and alertness.
ii. Recurrent visual hallucinations which are typically well formed and detailed.
iii. Spontaneous motor features of parkinsonism.
c.) Features supportive of the diagnosis are:
i. Repeated falls
ii. Syncope
iii. Transient loss of consciousness
iv. Neuroleptic sensitivity
v. Systematised delusions
vi. Hallucinations in other modalities.
d.) A diagnosis of DLB is less likely in the presence of:
i. Stroke disease, evident as focal neurological signs or on brain imaging.
ii. Evidence on physical examination and investigation of any physical illness, or other brain disorder, sufficient to account for the clinical picture.

The individual may be suspected of being at risk of developing DLB because of the presence of one or more factors which increase susceptibility to DLB. The individual may have a familial history of DLB. For example, carrying ApoE epsilon 4 is a risk factor for DLB. Also, presenting mutations for glucocerebrosidase (GBA) represent a recognized genetic risk for synucleynopathies.

As a further example, the patient may exhibit one or more symptoms associated with AD, including lapses of memory and problems finding the right words during speech, confusion, irritability and aggression, delusions, paranoia, mood swings, language breakdown, long-term memory loss, and general withdrawal. Typically, the patient may exhibit one or more of the NINCDS-ADRDA criteria for the clinical diagnosis of probable AD, which are as follows:

Definite Alzheimer's disease: The patient meets the criteria for probable Alzheimer's disease and has histopathologic evidence of AD via autopsy or biopsy.

Probable Alzheimer's disease: Dementia has been established by clinical and neuropsychological examination. Cognitive impairments also have to be progressive and be present in two or more areas of cognition. The onset of the deficits has been between the ages of 40 and 90 years and finally there must be an absence of other diseases capable of producing a dementia syndrome.

Possible Alzheimer's disease: There is a dementia syndrome with an atypical onset, presentation or progression; and without a known etiology; but no co-morbid diseases capable of producing dementia are believed to be in the origin of it.

Unlikely Alzheimer's disease: The patient presents a dementia syndrome with a sudden onset, focal neurologic signs, or seizures or gait disturbance early in the course of the illness.

The individual may be suspected of being at risk of developing AD because of the presence of one or more factors which increase susceptibility to AD. The individual may have a familial history of AD. For example, the individual may have a family history of dementia in a first degree relative (sibling or parent), and mutations in genes including amyloid precursor protein (APP), presenilin 1 and presenilin 2. ApoE epsilon 4 is risk factor for late AD.

As a further example, the individual may exhibit one or more symptoms associated with FTD. The symptoms of FTD can be classified (roughly) into two groups which underlie the functions of the frontal lobe: behavioural symptoms (and/or personality change) and symptoms related to problems with executive function. Behavioural symptoms include lethargy and aspontaneity or oppositely disinhibition. Apathetic patients may become socially withdrawn and stay in bed all day or no longer take care of themselves. Disinhibited patients can make inappropriate (sometimes sexual) comments or perform inappropriate acts. Patients with FTD can sometimes get into trouble with the police because of inappropriate behaviour such as stealing. Recent findings indicate that psychotic symptoms are rare in FTD, possibly due to limited temporal-limbic involvement in this disorder. Among the FTD patients, only 2 (2.3%) had delusions, 1 of whom had paranoid ideation; no FTD patient had hallucinations. This was significantly less than the AD patients, (17.4%) of whom had delusions and paranoia. Executive function is the cognitive skill of planning and organizing. Patients become unable to perform skills that require complex planning or sequencing. Typically, the patient may or may not have been assessed using (or have been diagnosed using) the Lund-Manchester criteria for the clinical diagnosis of FTD, which require the presence of at least two of the following features: loss of personal awareness, strange eating habits, perseveration, and mood change. In addition, patients must have one or more of the following: frontal executive dysfunction, reduced speech, and preserved visuospatial ability. The criteria also refer to several important supporting features, including onset before age 65, a family history of FTD, early urinary incontinence, motor neuron disease, and (in the late stages) akinesia, rigidity, and tremor.

The individual may be suspected of being at risk of developing FTD because of the presence of one or more factors which increase susceptibility to FTD. The individual may have a familial history of FTD. For example, approximately 20-50% of individuals with frontotemporal dementia (FTD) have an affected first-degree-relative. Changes in the following five genes have been identified: MAPT gene on chromosome 17 that makes the protein tau; GRN gene, also called the PGRN gene, on chromosome 17 that makes progranulin protein; TARDBP gene on chromosome 1 that produces transactive response DNA-binding protein of 43-kDa molecular weight (TDP-43); VCP gene on chromosome 9 that codes for valosin-containing protein; and CHMP2B gene on chromosome 3 that expresses charged multivesicular body protein 2B (also known as chromatin modifying protein 2B). Mutations in the MAPT and GRN genes on chromosome 17 are the most common genetic causes of FTD.

The patient may or may not have been assessed using the Mini-mental state examination (MMSE—*Journal of Psychiatric Research* 1975; 12 (3): 189-98) or other clinical test for assessing dementia such as the Milan Overall Dementia Assessment (MODA—*J Neurol Neurosurg Psychiatry* 1994; 57: 1510-17). Using the MMSE, any score over 27 (out of 30) is effectively normal. Below this, 20-26 indicates some cognitive impairment; 10-19 moderate to severe cognitive impairment, and below 10 very severe cognitive impairment. The raw score may also be corrected for degree of schooling and age. Low to very low scores correlate closely with the presence of dementia. Typically the patient in the method of the invention will have an MMSE score in the range 15-30

The present invention involves measuring the concentration of α-syn and the concentration of tau protein in a cerebrospinal fluid (CSF) sample taken from an individual. The invention may measure the total concentration of tau protein, wherein the total concentration is the concentration of phosphorylated tau (p-tau) added to the concentration of unphosphorylated tau (tau). Alternatively, only the concentration of α-syn and the concentration of p-tau may be measured. The ratio of α-syn to total tau or to p-tau is then calculated. By concentration, it is meant the quantity of a given marker per unit volume. For example, the concentrations of the invention may typically be measured in units of ng/ml.

According to the present invention, a ratio of total tau to α-syn of less than 20:1, 19.5:1, 19:1, 18.5:1, 18:1, 17.5:1 or 17:1 is indicative that the patient has PD rather than a different neurodegenerative disorder which is not PD. Preferably the ratio is less than 18.5:1.

According to the present invention, a ratio of p-tau to α-syn of less than 5:1, 4.5:1, 4:1, 3.5:1, 3:1, 2.5:1 or 2:1 is indicative that the patient has PD rather than a different neurodegenerative disorder which is not PD. Preferably the ratio is less than 3.1:1.

According to the present invention, a decreased ratio of α-syn to total tau or to p-tau compared with the ratio in a sample from a patient with AD, DLB or FTD indicates that the individual has PD rather than a different neurodegenerative disorder which is not PD.

For example the ratio of total tau or to p-tau to α-syn in a sample from a PD patient may be decreased by at least 1.5 fold, at least 2 fold, at least 2.5 fold, at least 3 fold, at least 4 fold or at least 5 fold relative to the ratio in a sample from a patient with AD, DLB or FTD.

According to the present invention, a ratio of total tau or to p-tau to α-syn which is not significantly different to the ratio in a sample from a normal individual indicates that the individual has PD rather than a different neurodegenerative disorder which is not PD.

For example, the ratio of total tau or to p-tau to α-syn in a sample from a PD patient may differ from the ratio in a sample from a normal patient by no more than 5%, 10%, 15%, 20% or 25%.

A normal patient or individual is an individual categorised as cognitively or neurologically normal. Preferably the normal individual is age-matched to the individual to be tested.

The invention is typically carried out in vitro on a cerebrospinal fluid (CSF) sample obtained from the individual. The sample may be typically processed prior to being assayed, for example by centrifugation. The sample may also be stored prior to assay, preferably below −70° C.

Standard methods known in the art may be used to assay the level of α-syn, tau and p-tau. These methods typically involve using an agent for the detection of the relevant protein. The agent typically binds specifically to said protein. The agent may be an antibody specific for the protein. By specific, it will be understood that the agent or antibody binds to α-syn, tau or p-tau with no significant cross-reactivity to any other molecule, particularly any other protein, most particularly any of the other proteins listed. For example, an agent or antibody specific for α-syn will show no significant cross-reactivity with tau or p-tau. An agent or antibody specific for p-tau will show no significant cross-reactivity with α-syn or tau. Cross-reactivity may be assessed by any suitable method.

Protein levels are measured using any conventional method. A preferred method is a conventional sandwich ELISA assay. That is, wherein the capture and detection antibodies are antibodies which are specific for the same protein but bind to different epitopes on that protein. Ideally, the form of the "read out" for the method for measuring each protein should be the same. This facilitates calculation of the ratios of the method of the invention. The "read out" of a given assay will typically be converted into a concentration level by using a standard curve generated by testing samples of known concentration in the assay.

An antibody used in any method of the invention may either be a whole antibody or a fragment thereof which is capable of binding to the desired protein. The antibody may be monoclonal. Such a whole antibody is typically an antibody which is produced by any suitable method known in the art. For example, polyclonal antibodies may be obtained by immunising a mammal, typically a rabbit or a mouse, with the target protein under suitable conditions and isolating antibody molecules from, for example, the serum of said mammal. Monoclonal antibodies may be obtained by hybridoma or recombinant methods.

Typically the antibody is a mammalian antibody, such as a primate, human, rodent (e.g. mouse or rat), rabbit, ovine, porcine, equine or camel antibody. The antibody may be a camelid antibody or shark antibody. The antibody may be a nanobody. The antibody can be any class or isotype of antibody, for example IgM, but is preferably IgG. The fragment of whole antibody that can be used in the method comprises an antigen binding site, e.g. Fab or F(ab)2 fragments. In one embodiment the antibody is a chimeric antibody comprising sequence from different natural antibodies, for example a humanised antibody.

The invention further provides a diagnostic kit that comprises means for measuring the level of α-syn, tau and p-tau in a sample, and thereby determining whether or not the individual has PD. The kit typically contains one or more antibodies that specifically bind the above proteins. For example, the kit may comprise a monoclonal antibody, a polyclonal antibody, a single chain antibody, a chimeric antibody, a CDR-grafted antibody or a humanized antibody. The antibody may be an intact immunoglobulin molecule or a fragment thereof such as a Fab, F(ab')$_2$ or Fv fragment.

The kit may additionally comprise one or more other reagents or instruments which enable any of the embodiments of the method mentioned above to be carried out. Such reagents or instruments include one or more of the following: suitable buffer(s) (aqueous solutions), means to isolate α-syn, tau or p-tau from a sample, means to obtain a sample from the individual (such as a vessel or an instrument comprising a needle) or a support comprising wells on which quantitative reactions can be done. The kit may, optionally, comprise instructions to enable the kit to be used in the method of the invention or details regarding which individuals the method may be carried out upon.

The invention also provides a method of delaying or preventing the onset of PD symptoms in an individual. The method comprises: (i) determining whether or not an individual has PD using a method according to the invention; and (ii) administering to an individual identified as having PD in (i), a therapeutically effective amount of an agent that directly or indirectly inhibits α-syn aggregation and/or toxicity, an agent that reduces expression of the α-syn protein, an agent that directly or indirectly enhances or stimulates the degradation of α-syn aggregates, or a neuroprotective agent. The neuroprotective agent is typically an anti-apoptotic, an antioxidant, an anti-glutamatergic, a monoamine oxidase B inhibitor, an adenosine antagonist, a dopamine agonist, a mitochondrial stabiliser or a trophic factor. For example, the neuroprotective agent may be rasagiline, selegiline, ropinirole, pramipexole, nicotine, minocycline, creatine, caffeine, or coenzyme Q10.

The following Example illustrates the invention:

EXAMPLE

Methods

Patients

The subjects included in this study were prospectively recruited in the period June 2005-April 2009. They represent a consecutive series of patients referred to our Centre for diagnostic evaluation. All of them were thoroughly assessed including accurate neuropsychological testing, neuroimaging (CT/MRI) and lumbar puncture. CSF was collected in Day-Service regimen, according to the hospital standard protocol and with the local Ethical Committee approval, after informed written consent was given by the patient or the relative/caregiver, in case of subjects with dementia. Idiopathic PD was diagnosed according to United Kingdom Parkinson's Disease Society Brain Bank. All of them were treated with L-dopa alone or associated to dopamine agonists, with good control of motor symptoms (mean UPRDS-III: 20.2±5.3), and were functionally independent (Hoehn and Yahr 1-3). None of them showed clinically relevant signs of cognitive impairment. Probable DLB was defined according to McKeith's criteria. Patients underwent a thorough clinical and neurological evaluation including neuropsychological assessments (MMSE and MODA), psychobehavioral assessment (NeuroPsychiatric Inventory) and fluctuations assessment, as well as brain magnetic resonance imaging (MRI) for excluding vascular damages or other lesions. SPECT DAT-Scan was carried out in 24 DLB patients, and putaminal hypocaptation was observed in all of them. Twenty-seven out of thirty-two DLB patients exhibited extrapyramidal symptoms at the onset of dementia (mean UPRDS-III: 18.9±8.3), and visual hallucinations were present in 29 of them. Cognitive fluctuations occurred in all DLB patients. Alzheimer's disease was diagnosed according to the NINCDS-ADRDA criteria for probable AD. FTD was diagnosed according to Lund-Manchester criteria. In this group, 12 patients had the clinical onset as progressive non-fluent aphasia, 5 showed a semantic dementia and 14 were clinically defined as frontal variant. All of them underwent either SPECT or PET as supportive criterion. None of them showed relevant signs of parkinsonism at onset. As control group, cognitively normal age-matched subjects who underwent lumbar puncture as a part of diagnostic work-up for other neurological conditions (OND)—headache or suspected myelopathy—were recruited. Thus OND refers to cognitively normal controls.

CSF Sampling

Lumbar puncture has been performed between 08.00 and 10.00 a.m., after an overnight fast. CSF (10 mL) was collected in sterile polypropylene tubes, centrifuged for 10 minutes at 4000 g and 0.5 mL aliquots were immediately frozen at −80° C. CSF levels of the "classical biomarkers" β amyloid$_{1-42}$ (Aβ42), total tau, and p-tau were measured using standard ELISA methods (Innotest β amyloid$_{1-42}$, hTAU-Ag, p-TAU 181 Ag, Innogenetics NV, Gent, Belgium).

Immunoassay for α-Synuclein in CSF

Total α-syn in the CSF samples was measured using a sandwich ELISA assay with some modification to improve the sensitivity of the assay to measure α-syn directly from the CSF samples. An anti-human α-syn monoclonal antibody 211 (Santa Cruz Biotechnology, USA) was used for capturing, and anti-human α-syn polyclonal antibody FL-140 (Santa Cruz Biotechnology, USA) was used for antigen detection through a horseradish peroxidase (HRP)-linked chemiluminescence assay. ELISA plate (Nunc Maxisorb, NUNC, Denmark) was coated for overnight incubation at 4° C., with 1 μg/ml of 211 (100 μl/well), in 200 mM NaHCO3, pH 9.6. After incubation for 2 hours with 200 μl/well of blocking buffer (phosphate-buffered saline (PBS) containing 2.5% gelatin and 0.05% Tween 20), 100 μl of the CSF samples were then added to each well and incubated at 37° C. for 3 hrs. After the incubation, captured α-syn protein was detected by the reaction with 100 μl/well of FL-140 antibody (0.2 μg/ml), followed by incubation with 100 μl/well (1:10, 000-dilution) of horseradish peroxidase (HRP)-labeled anti-rabbit antibody (DAKO, Denmark). Bound HRP activities were assayed by (100 μl/well) chemiluminescent reaction using an enhanced chemiluminescent substrate (SuperSignal ELISA Femto Maximum Sensitivity Substrate, Pierce Biotechnology, Rockford, USA). The chemiluminescence in relative light units was measured at 395 nm with a microplate luminometer (SpectraMax L, Molecular Device, Tokyo). The standard curve for the ELISA assay was carried out using 100 μl/well of recombinant human α-syn solution at different concentrations of the protein in PBS. All samples and standards were run in triplicate on the same day with the same lot of standards. The relative concentration estimates of total α-syn in CSF were calculated according to each standard curve. The intra-assay and inter-assay coefficient of variation was <10%. For all ELISA assays, samples were constantly kept on ice. The assays were performed on sample aliquots never thawed before.

Statistical Analysis

Results are expressed as mean±SD, unless otherwise indicated. All data were log-transformed for the purpose of statistical analysis; comparisons between groups were performed using the one-way ANOVA and the Student-Newman Keuls as a post-hoc test. Correlations are expressed as Pearson's correlation coefficient. Diagnostic accuracy has been assessed by means of Receiver Operating Characteristic, ROC, analysis.

Results

Figure 2:
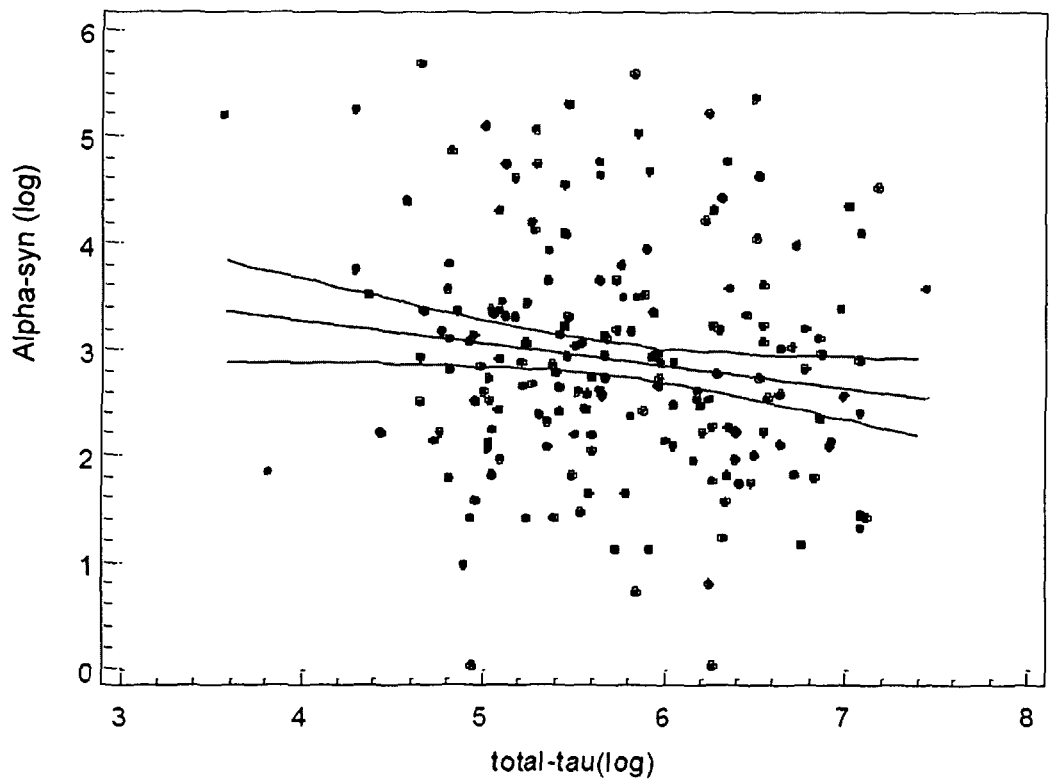
FIG. 2 shows a regression line and 95% confidence limits of total tau vs α-syn (log-transformed) in the whole group studied.
Figure 3:
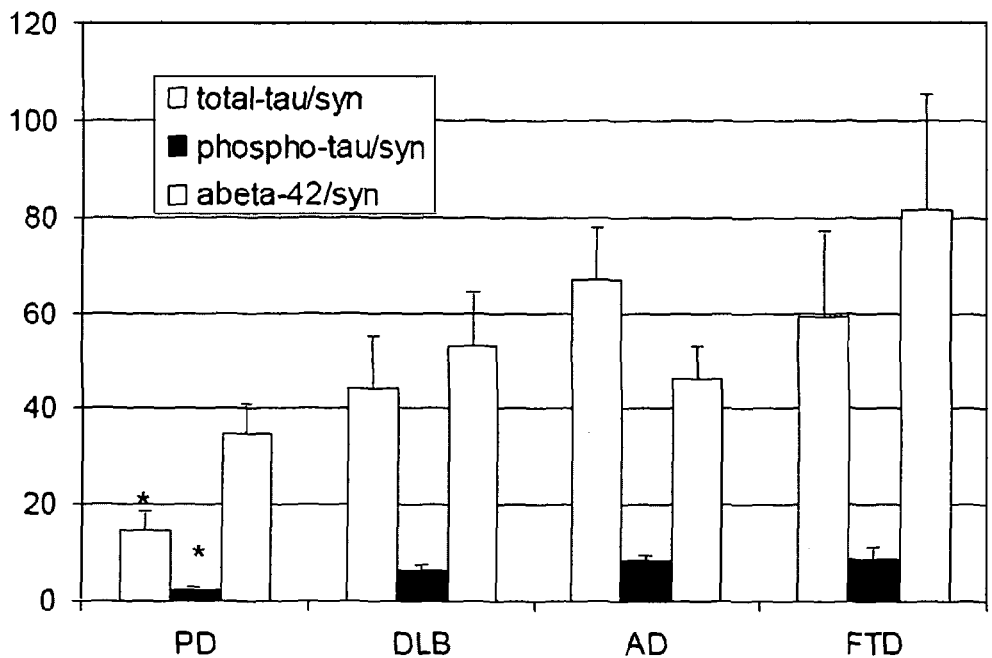
FIG. 3 shows the distribution of the indicated CSF marker ratios (mean±SEM) in subjects with Parkinson's Disease (PD), Dementia with Lewy bodies (DLB), Alzheimer's Disease (AD), Frontotemporal Dementia (FTD). * indicates where a significant difference was observed for a given group versus the other pathological groups.
Figure 4:
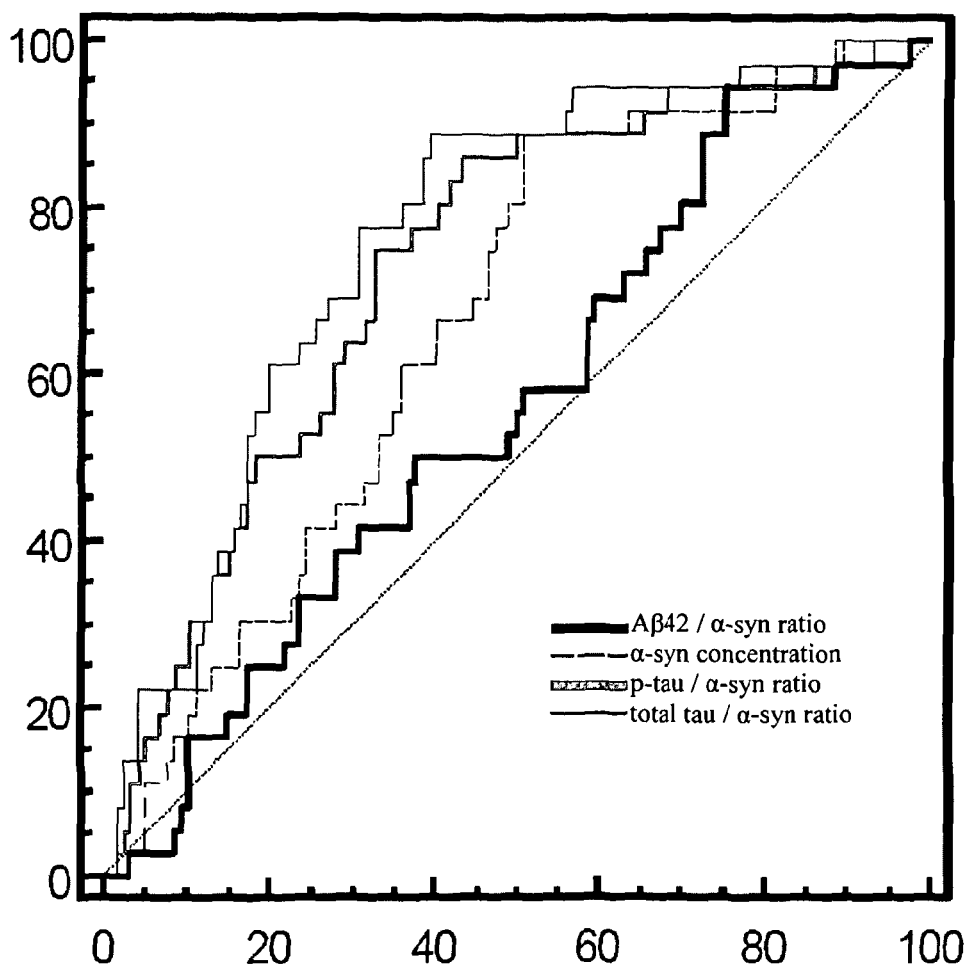
FIG. 4 shows Receiver Operating Characteristic (ROC) curves for values in CSF samples from PD subjects for the total tau/α-syn ratio (thin, solid line—tending to top left of Figure), the Aβ42/α-syn ratio (thick dark line—tending to bottom right of Figure), the p-tau/α-syn ratio (thick, light grey line—tending towards top left, generally below the total tau/α-syn line), and the α-syn concentration alone (thin dashed line—tending between the p-tau & total tau/α-syn lines and the Aβ42/α-syn line).

Demographic details are reported in Table 1. The groups did not differ with respect to mean age and schooling. Mean MMSE score did not significantly differ between PD group and controls. However, in neuropsychological tests assessing executive functions (verbal fluency, attention, working memory) they generally obtained lower scores with respect to age matched controls. Finally, the dementia groups showed comparable degree of cognitive deterioration and duration of disease. FIG. 1 shows the scatter of CSF α-syn values observed in each group, while in Table 2 the mean values of CSF parameters are reported. All pathological groups showed significantly lower mean CSF α-syn levels with respect to controls (other neurological diseases, OND), where DLB and FTD disclosed the lowest values (FIG. 1). CSF mean levels of classical biomarkers were substantially similar in PD and controls, while in the dementia groups they were significantly altered. Aβ42 was significantly lower in AD, DLB, FTD vs OND and PD. Analogously, mean CSF total tau levels were higher in the dementia groups as compared to OND and PD; as expected, the highest values of total tau were observed in AD group, differentiating this category from the other dementia groups (Table 2). Also CSF p-tau showed the highest mean levels in AD, being significantly higher in all dementia categories with respect to OND and PD, as well. α-syn showed an inverse correlation with age (1=−0.19, p=0.011) and duration of disease (r=−0.15, p=0.08). No association with MMSE scores was detected. With respect to the classical biomarkers, a significant inverse correlation with total tau (r=−0.21, p=0.007) was documented (FIG. 2). No significant correlation was found with Aβ42 and p-tau. Finally, total-tau and p-tau showed a significant positive correlation with duration of disease (r=0.27, p=0.001, p=0.005, respectively), while Aβ42 did not. The performance of the ratios Aβ42/α-syn, total tau/α-syn and p-tau/α-syn in discriminating the groups studied was evaluated (Table 3, FIG. 2). Total tau/α-syn and p-tau/α-syn ratios were significantly lower in PD with respect to all the other pathological groups considered, including DLB (Table 3). In order to calculate the sensitivity and specificity of these ratios in discriminating PD from the other pathological conditions, we then performed the Receiver Operating Characteristic (ROC) analysis (Table 4. FIG. 3). As expected, CSF α-syn alone did not provide relevant information for PD diagnosis, showing extremely poor specificity relative to other neurological disorders. A better performance was obtained with the total tau/α-syn ratio: at the cut-off of 19.5:1 (AUC: 0.765), sensitivity was 89% and specificity 61%. p-tau/α-syn ratio disclosed slightly lower results.

Conclusions

The ratios between CSF tau and α-syn have shown differences occurring among the clinical entities considered. PD had CSF tau/α-syn ratio similar to that observed in control subjects. Conversely, all the other pathological groups, including DLB, had similarly high values of both total tau/α-syn and p-tau/α-syn ratios (Table 3, FIG. 3). Such ratios showed a good sensitivity (>85%) but lower specificity (55-61%) in discriminating PD from the other conditions. This information provides a valuable indicator for the early diagnosis of PD.

Tables

Mean values are shown ±SD unless indicated otherwise. τ=total tau, P-τ=p-tau.

TABLE 1

Demographic details of the subjects studied

|  | PD (n = 38) | DLB (n = 32) | AD (n = 48) | FTD (n = 31) | OND (n = 32) |
|---|---|---|---|---|---|
| M/F | 22/16 | 18/14 | 19/29 | 17/14 | 18/14 |
| Age (yr)* | 69.3 ± 7.2 | 71.4 ± 6.0 | 68.7 ± 9.7 | 64.3 ± 6.4 | 61.9 ± 17.8 |
| Duration (yr)* | 3.5 ± 2.3 | 3.9 ± 2.7 | 4 ± 2.9 | 4.2 ± 2.2 | = = |
| MMSE score* | 25.9 ± 2.4 | 15.5 ± 2.9 | 16.6 ± 4.4 | 18.9 ± 3.7 | 28.0 ± 1.7 |
| Schooling (yr)* | 8.4 ± 3.1 | 8.1 ± 4.4 | 7.1 ± 3.3 | 7.0 ± 3.5 | 7.4 ± 4 |

TABLE 2

Mean values of CSF α-syn, Aβ42, total tau and p-tau in the groups studied

Multiple comparisons: P < 0.05 a: vs OND; b: vs PD; c: vs AD; d: vs DLB; e: vs FTD; f: vs other

|  | PD (n = 38) | DLB (n = 32) | AD (n = 48) | FTD (n = 32) | OND | P |
|---|---|---|---|---|---|---|
| α-syn (ng/mL) | 43.1 ± 47$^a$ | 18.1 ± 16$^{a,b,c}$ | 34.8 ± 54$^a$ | 15.3 ± 18$^{a,b,c}$ | 68.9 ± 71 | 0.001 |
| Aβ42 (pg/mL) | 658 ± 263 | 451 ± 209$^{a,b}$ | 481 ± 190$^{a,b}$ | 489 ± 146$^{a,b}$ | 624 ± 227 | 0.005 |
| Total τ (pg/mL) | 232 ± 164 | 341 ± 254$^{a,b}$ | 734 ± 357$^f$ | 424 ± 241$^{a,b}$ | 190 ± 96 | 0.001 |
| P-τ (pg/mL) | 41.6 ± 21 | 49.5 ± 26$^a$ | 97.7 ± 41$^f$ | 59.5 ± 40$^{a,b}$ | 35.3 ± 11 | 0.001 |

TABLE 3

CSF biomarker ratios according to diagnosis
Multiple comparisons: P < 0.05 a: vs OND; b: vs others

|  | PD (n = 38) | DLB (n = 32) | AD (n = 48) | FTD (n = 31) | OND (n = 32) | P |
|---|---|---|---|---|---|---|
| Aβ42/α-syn | 34.7 ± 38 | 53.1 ± 49 | 46.1 ± 45 | 81.6 ± 91 | 27.9 ± 32 | 0.08 |
| Total τ/α-syn | 14.4 ± 24$^b$ | 42.7 ± 59$^a$ | 67 ± 76$^a$ | 60 ± 94$^a$ | 6.9 ± 6.6 | 0.002 |
| P-τ/α-syn | 2.3 ± 2.8$^b$ | 6.2 ± 7.8$^a$ | 8.2 ± 9.2$^a$ | 8.6 ± 12$^a$ | 1.4 ± 1.1 | 0.002 |

TABLE 4

ROC curve parameters for CSF marker ratios in PD patients.

|  | AUC | Optimal cut-off (ng/mL) | Sensitivity/specificity (%) |
|---|---|---|---|
| α-syn | 0.662 | 13.0 | 94/25 |
| Total τ/α-syn | 0.765* | 19.5 | 89/61 |
| P-τ/α-syn | 0.733* | 3.1 | 86/55 |
| Aβ42/α-syn | 0.586 | 61.8 | 87/57 |

*p = 0.001 vs α-syn and Aβ42/α-syn

The invention claimed is:

1. A method of identifying whether or not an individual has Parkinson's Disease (PD) rather than a neurodegenerative disease which is not PD, which method comprises:
   (i) measuring the concentration of α-synuclein (α-syn) in a cerebrospinal fluid (CSF) sample taken from the individual;
   (ii) measuring the concentration of unphosphorylated tau (tau) and/or phosphorylated (p-tau) present in the sample; and
   (iii) calculating the ratio of:

$$\frac{\text{total concentration of tau}}{\text{concentration of } \alpha\text{-syn}} \text{ or } \frac{\text{concentration of } p\text{-tau}}{\text{concentration of } \alpha\text{-syn}}$$

wherein the total concentration of tau is the cumulative concentration of p-tau and tau measured in the sample; and
   (iv) thereby determining whether or not the individual has PD according to at least one of the following:
      (a) a ratio of total tau to α-syn of 19.5:1 or less is indicative that the individual has PD rather than a neurodegenerative disease which is not PD; or
      (b) a ratio of p-tau to α-syn of 3.1:1 or less is indicative that the individual has PD rather than a neurodegenerative disease which is not PD; or
      (c) a decreased ratio of total tau to α-syn or p-tau to α-syn relative to the corresponding ratio in a sample taken from an individual having a neurodegenerative disease which is not PD, is indicative that the individual has PD rather than a neurodegenerative disease which is not PD; or
      (d) a ratio of total tau to α-syn or p-tau to α-syn that is not significantly different to the corresponding ratio in a sample taken from a normal individual is indicative that the individual has PD rather than a neurodegenerative disease which is not PD.

2. A method according to claim 1 wherein said determining is in accordance with step (iv)(c), and the individual is determined as having PD when the ratio of total tau to α-syn or p-tau to α-syn is decreased by at least 3 fold relative to the corresponding ratio in a sample taken from an individual having a neurodegenerative disease which is not PD.

3. A method according to claim 1, wherein said determining is in accordance with step (iv)(c), and the neurodegenerative disease which is not PD is Alzheimers Disease (AD), Dementia with Lewy bodies (DLB) or Fronto-temporal Dementia (FTD).

4. A method according to claim 1 wherein said determining is in accordance with step (iv)(d), and the ratio of total tau to α-syn or p-tau to α-syn differs by no more than 25% relative to the corresponding ratio in a sample taken from a normal individual.

5. A method according to claim 1, wherein the individual is suspected of being at risk of developing a neurodegenerative disorder.

6. A method according to claim 5, wherein the individual has a familial history of a neurodegenerative disorder.

7. A method according to claim 5, wherein the individual has or has been diagnosed with a clinical symptom associated with a diagnosis of a neurodegenerative disorder.

8. A method according to claim 5, wherein the neurodegenerative disorder is PD, AD, DLB or FTD.

9. A method according to claim 5, wherein the individual is categorised as Hoehn-Yahr grade 3 or lower.

10. A method according to claim 5, wherein the individual is categorised as having a Mini-mental state examination (MMSE) score of 19 to 26.

* * * * *